(12) United States Patent
Karvonen

(10) Patent No.: US 8,790,220 B2
(45) Date of Patent: Jul. 29, 2014

(54) INTERFACE CIRCUITRY FOR GYM APPARATUS

(71) Applicant: Polar Electro Oy, Kempele (FI)

(72) Inventor: Sami Karvonen, Travers (CH)

(73) Assignee: Polar Electro Oy, Kempele (FI)

(*) Notice: Subject to any disclaimer, the term of this patent is extended or adjusted under 35 U.S.C. 154(b) by 0 days.

(21) Appl. No.: 14/081,769

(22) Filed: Nov. 15, 2013

(65) Prior Publication Data

US 2014/0142732 A1    May 22, 2014

(30) Foreign Application Priority Data

Nov. 16, 2012    (GB) .................................. 1220629.8

(51) Int. Cl.
A63B 24/00    (2006.01)

(52) U.S. Cl.
USPC ........................ 482/8; 482/1; 482/9; 482/901

(58) Field of Classification Search
USPC ............................ 482/1–9, 900–902; 434/247
See application file for complete search history.

(56) References Cited

U.S. PATENT DOCUMENTS

| | | | | |
|---|---|---|---|---|
| 8,172,724 | B2* | 5/2012 | Solomon | 482/8 |
| 8,419,593 | B2* | 4/2013 | Ainsworth et al. | 482/8 |
| 8,568,278 | B2* | 10/2013 | Riley et al. | 482/9 |
| 2009/0181826 | A1 | 7/2009 | Turner | |
| 2012/0157265 | A1 | 6/2012 | Kao | |
| 2012/0184823 | A1 | 7/2012 | Chen | |
| 2012/0264568 | A1 | 10/2012 | Allowitz-Thompson | |

FOREIGN PATENT DOCUMENTS

| | | |
|---|---|---|
| CN | 102462931 A | 5/2012 |
| CN | 202315109 U | 7/2012 |
| EP | 2 389 009 A2 | 11/2011 |
| WO | 00/69525 A1 | 11/2000 |
| WO | 2008/036275 A2 | 3/2008 |
| WO | 2012/054818 A2 | 4/2012 |

OTHER PUBLICATIONS

United Kingdom Office Action dated Sep. 18, 2013, Application No. GB1220629.8, 3 pages.
United Kingdom Office Action dated Jun. 7, 2013, Application No. GB1220629.8, 4 pages.
United Kingdom Office Action dated Mar. 4, 2013, Application No. GB1220629.8, 4 pages.
United Kingdom Office Action dated Dec. 12, 2012, Application No. GB1220629.8, 8 pages.
International Search Report, Application No. PCT/FI2013/051073, Feb. 17, 2014, Authorized Officer Tuomo Reiniaho, 5 pages.

* cited by examiner

Primary Examiner — Glenn Richman
(74) Attorney, Agent, or Firm — Hoffmann & Baron, LLP

(57) ABSTRACT

An interface circuitry for a gym apparatus and the gym apparatus are disclosed. The interface circuitry comprises: a power transmission system interface to a power transmission system of the gym apparatus; a sensor interface to one or more sensors comprised in the gym apparatus and/or one or more sensors external to the gym apparatus; and a user interface connector connecting the interface circuitry to a casing of a portable electronic device serving as a user interface of the gym apparatus during a physical exercise performed with the gym apparatus. The interface circuitry includes a processing system arranged to cause the interface circuitry to process and provide connections between the power transmission system interface, sensor interface, and the user interface connector.

16 Claims, 4 Drawing Sheets

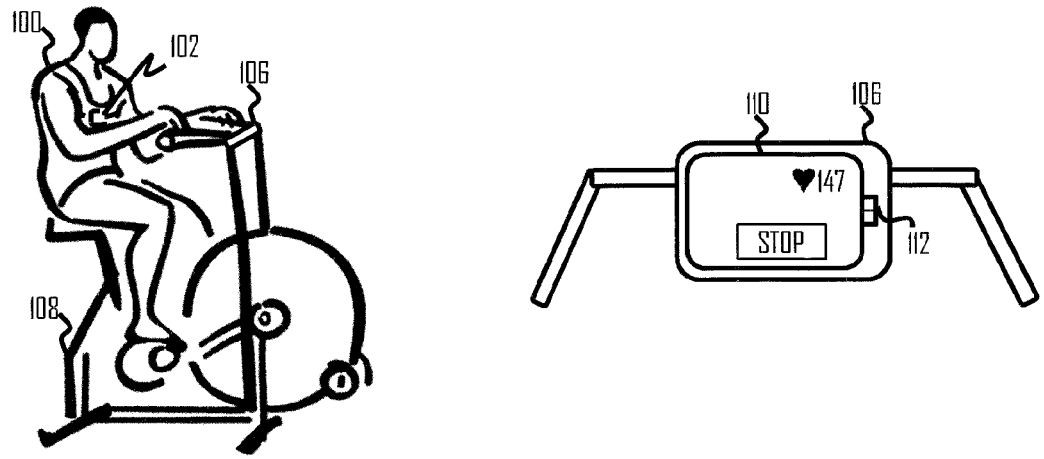
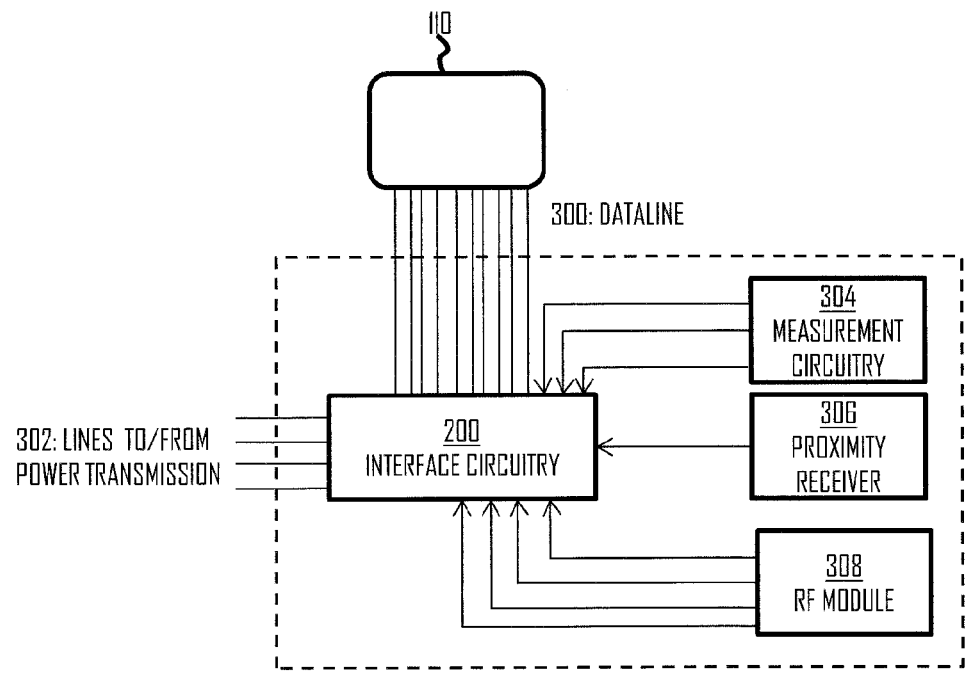
Fig 1
Fig 3A

INTERFACE CIRCUITRY FOR GYM APPARATUS

CROSS-REFERENCE TO RELATED APPLICATIONS

This application claims priority to United Kingdom Application No. 1220629.8, filed 16 Nov. 2012, which is incorporated by reference herein in its entirety.

FIELD

The present invention relates to the field of gym equipment and, particularly, to an interface circuitry comprised in a gym apparatus.

DESCRIPTION OF THE RELATED ART

Modern electronic gym equipment such as treadmills, exercise bicycles, and cross trainers comprise a user interface to receive commands from the user and to output information related to a physical exercise to the user. The user interface may comprise a display unit, a touch-sensitive display, buttons, etc.

SUMMARY

According to the present invention, there is provided a gym apparatus comprising: an interface circuitry realized on a single circuit board and comprising: a processing system; a power transmission system interface for a power transmission system of said gym apparatus; a sensor interface for one or more sensors comprised in said gym apparatus, the sensor interface comprising: a measurement circuitry comprising hand measurement electronics including a differential amplifier, a signal path to the processing system of the interface circuitry, and filtering; and a radio frequency module arranged to establish a radio connection with a heart rate sensor external to a said gym apparatus and attachable to a user's body; and a standardized user interface connector for connecting the interface circuitry to a casing of a portable electronic device serving as a user interface of said gym apparatus during a physical exercise performed with said gym apparatus, wherein said processing system is constructed and arranged to cause the interface circuitry to process and provide connections between the power transmission system interface, the sensor interface, and the user interface connector, and wherein said portable electronic device is integrated into the gym apparatus and comprises: a communication interface arranged to connect to the standardized user interface connector, a user interface comprising a touch-sensitive display, and an internet browser supporting web applications.

The processing system described above may comprise at least one processor and at least one memory including a computer program code, wherein the at least one memory and the computer program code are configured, with the at least one processor, to cause the interface circuitry to operate as described above.

Further features and advantages of the invention will become apparent from the following description of preferred embodiments of the invention, given by way of example only, which is made with reference to the accompanying drawings.

BRIEF DESCRIPTION OF THE DRAWINGS

FIG. 1 illustrates schematically an example of a gym apparatus and its user interface according to an embodiment of the invention;

FIGS. 3A and 3B illustrate schematically detailed block diagrams of an example of connectivity provided by the interface circuitry according to some embodiments of the invention.

DETAILED DESCRIPTION

Figure 2A:
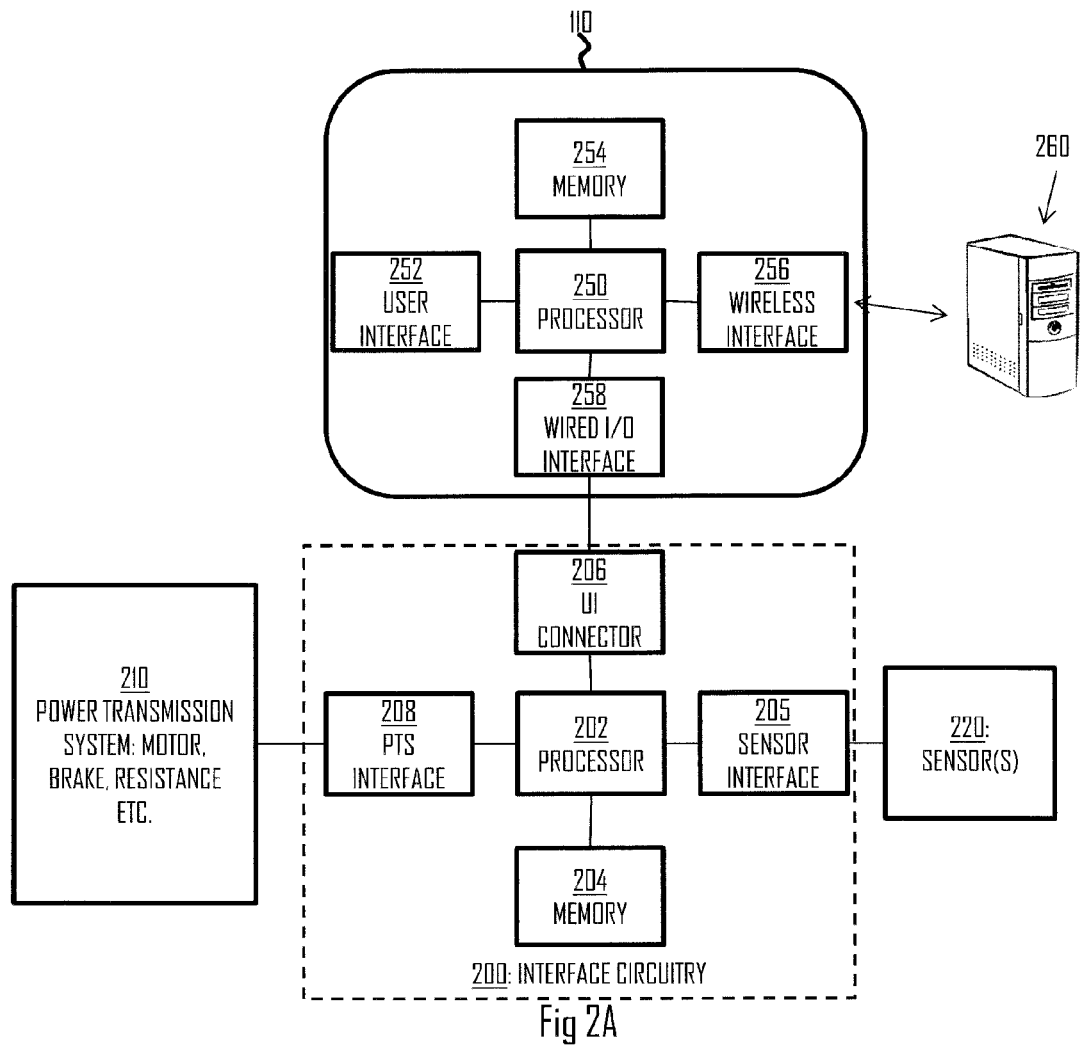
FIGS. 2A and 2B illustrate block diagrams of structures of an example of an interface circuitry suitable for the gym apparatus and an example of a portable electronic device connected to the interface circuitry according to an embodiment of the invention.

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

FIG. 1 illustrates schematically an example of a gym apparatus 108 according to an embodiment of the invention and an illustration of its handlebar to which a user interface of the gym apparatus 108 is attached. It should be appreciated that the user interface may be attached to any other location of the gym apparatus, depending on the design and the type of the gym apparatus.

Referring to FIG. 1, a user 100 carries out a physical exercise in a gym or in a similar training environment by using the gym apparatus 108, e.g. a treadmill, an exercise cycle, a rowing machine, etc. A user interface device 110 is attached to or integrated into the gym apparatus 108 to display various information related to the physical exercise. Referring to FIG. 1, the displayed information may comprise for example the user's heart rate and performance so far in terms of distance or energy consumption, and/or it may comprise input buttons enabling the user to configure the gym apparatus 108 and control the execution of the physical exercise. The user interface device 110 may comprise a touch-sensitive display. The user interface device 110 may be attached to a socket 106 comprised in the gym apparatus 108, and the socket may comprise an electric connector 112 connecting electronic circuitries of the gym apparatus 108 to the user interface device 110.

In an embodiment, the user interface device 110 is a portable electronic device connected to the gym apparatus 108 through a standardised connector, e.g. universal serial bus (USB), Firewire, Ethernet, high-definition multimedia interface (HDMI), RS-232, RS-485, $I^2C$. In an embodiment, the standardised connector provides for a bidirectional communication between the portable electronic device 110 and the gym apparatus 108. The physical form of the electric connector 112 may be a mini USB connector or any other dock connector that is commonly used as a data connector to connect an appliance to a tablet computer, a palm computer, or a mobile phone, etc. In this case, the appliance is the gym apparatus 108 and the portable electronic device 110 is the tablet computer, palm computer, or mobile phone or the like.

In general, the portable electronic device 110 may be a device that may be purchased by a private user as a stand-alone device.

A measurement device 102 is attached to the user's body to measure physiological data during the exercise. The measurement device 102 may be a heart rate sensor comprising at least one sensor to measure a heart rate of the user 100. The measurement device 102 may transmit measured heart rate measurement data wirelessly to the gym apparatus 108 and/or to a user's personal user interface device, e.g. the portable electronic device 110 or a user interface device worn by the user. An example of the worn user interface device is a wrist-worn computer. A wireless transmission may utilise one of the following short range device-to-device communication technologies: Bluetooth, Bluetooth Low Energy, Polar-compatible magnetic pulse operating on 5 kHz radio band, ANT or ANT+ by Dynastream, or IEEE 802.15.4. Other short-range device-to-device or network communication protocols are equally possible. The short range device-to-device connection may also be called a proximity connection because of its short communication range. The communication range may be in the order of a couple of meters, e.g. less than five meters.

In order to enable the interoperation between the gym apparatus 108 and the portable electronic device 110, an interface circuitry for the gym apparatus is provided. FIG. 2A illustrates a block diagram of an example of interface circuitry 200 suitable for the gym apparatus 108. Additionally, FIG. 2A illustrates components of the gym apparatus 108, e.g. a power transmission system 210 and optional sensors 220, and it illustrates a block diagram of the portable electronic device 110. The interface circuitry comprises a power transmission system (PTS) interface 208 to the power transmission system 210 of the gym apparatus. The power transmission system 210 may comprise any components that relate to the mechanics of the gym apparatus 108. The power transmission system 210 may comprise a motor, brakes, resistance, components affecting physical resistance to the power input applied by the user 100, gears, etc.

In an embodiment, the interface circuitry 200 further comprises a sensor interface 205 connecting to one or more sensors 220 comprised in the gym apparatus 108 and/or one or more sensors 220 external to the gym apparatus 108. The sensors 220 may comprise the measurement device 102 which the user is wearing.

In an embodiment, the interface circuitry 200 further comprises a user interface connector 206 of the above-mentioned standardised communication interface connecting the interface circuitry 200 to a casing of the portable electronic device 110 serving as the user interface of the gym apparatus 108.

in an embodiment, the interface circuitry 200 further comprises at least one processor 202 and at least one memory 204 including a computer program code configuring the operation of the processor 202 and the interface circuitry 200. The at least one processor 202, the at least one memory 204 and the computer program code configure the interface circuitry 200 to route the signals between the sensor(s) 220, the portable electronic device 110, and the power transmission system 210 of the gym apparatus 108. The interface circuitry 200 may carry out data format conversion between the different interfaces. For example, the standardised connection of the user interface connector 206 may require a data format complying with the specification of the applied standard.

FIG. 2A illustrates an embodiment where the processor 202, the user interface connector 206, the PTS interface 208, and the sensor interface 205 are comprised in the same structure to form the interface circuitry. They may be components assembled in the same casing or on the same circuit board, or otherwise contribute to the same structural entity of the interface circuitry 200. This is illustrated in FIG. 2A by the dashed line encircling the components 202 to 208 of the interface circuitry 200. In another embodiment illustrated in FIG. 2B, the components 202 to 208 of the interface circuitry 200 may be provided as structurally separate, e.g. in different casings or on different circuit boards.

The use of the standardised connection enables connection of commercially available portable electronic devices such as a tablet computer or a mobile phone to the gym apparatus. In an embodiment, the portable electronic device 110 may be attached detachably to the gym apparatus 108, thus enabling the user to attach his/her personal portable electronic device to the gym apparatus 108. Accordingly, the user may have readily available any training program and personal parameters for the physical exercise, and the user may easily bring the portable electronic device 110 from one gym apparatus to another. While the interface circuitry 200 may be integrated into a casing of the gym apparatus 108, the user interface connector 206 or a cable connected to the user interface connector 206 may be exposed such that the portable electronic device 110 may be connected electrically to the interface circuitry 200 to enable the portable electronic device 110 to communicate with the sensor(s) 220 and/or the power transmission system 210. The gym apparatus 108 may comprise a socket or a recession to receive and support the portable electronic device 110 during the physical exercise. The gym apparatus 108 may thus provide the portable electronic device 110 with a docking station to which the portable electronic device 110 may be easily attached. In an embodiment, a form of the socket or recession follows at least to some degree the form of a casing of the portable electronic device 110 such that the support is provided by the matching forms of the socket/recession and the casing.

In another embodiment, the portable electronic device 110 is integrated into the gym apparatus 108. The portable electronic device 110 may be fixed to the gym apparatus 108 during its manufacturing phase such that the removal or replacement of the portable electronic device 110 requires tools and a maintenance expert.

With respect to the definition of the portable electronic device 110, it should be appreciated that the portable electronic device 110 has the portability property as a stand-alone device. In the embodiments where the portable electronic device 110 is attached to the gym apparatus 108 detachably, the portability property is maintained. However, in the embodiments where the portable electronic device 110 is integrated into the gym apparatus, the portable electronic device may no longer be portable until it is detached or removed from the gym apparatus. In the context of the present specification, the word portability should thus be considered from that perspective in the description and in the claims. It should also be appreciated that the advantages of the portable electronic device 110 remain regardless of the level of integration. Furthermore, the portable electronic device 110 is operable in all embodiments regardless of whether or not it is attached/integrated into the gym apparatus. For example, when a tablet computer initially integrated into the gym apparatus 108 is removed from the gym apparatus 108, e.g. as a consequence of the gym apparatus breaking beyond repair, the tablet computer is still usable as the tablet computer. The same applies to other embodiments of the portable electronic devices, i.e. they may maintain their original operability and functions even if they are integrated into the gym apparatus 108. Conventional user interfaces of the gym apparatuses may only be used as spare parts. The portable electronic device 110 may have its original functions even when it is integrated or attached to the gym apparatus 108 and operates in cooperation with the gym apparatus 108 during the physical exercise. For example, the user may use the portable electronic device as the training user interface device and as an entertainment device, e.g. by launching an entertainment application that is executed concurrently with the application related to the physical exercise. The entertainment application may be an internet browser used for web browsing, a gaming application, a media player application such as a video or music player application, etc. The portable electronic device may then display on its display unit training data related to the physical exercise and the information related to the entertainment application. These information may be provided concurrently in a blended display.

An advantage provided by the use of the portable electronic devices and the standardised connections is that the user interface of the gym apparatus 108 may be realised by using commercially available solutions. One only needs to design the interface circuitry 202 and software application(s) executed in the portable electronic device 110. As the portable electronic devices such as tablet computers and mobile phones have an internet browser, the software applications related to the physical exercise performed with the gym apparatus may be designed by using web applications. A web application is a computer software application encoded in a programming language supported by the internet browsers, e.g. JavaScript combined with a browser-rendered mark-up language like hypertext mark-up language (html), and reliant on a common web browser to render the application executable. Web applications are also popular due to the convenience of using a web browser as client software, ability to update and maintain the web applications without distributing and installing software on potentially thousands of client computers, and the inherent support for cross-platform compatibility.

Figure 2B:
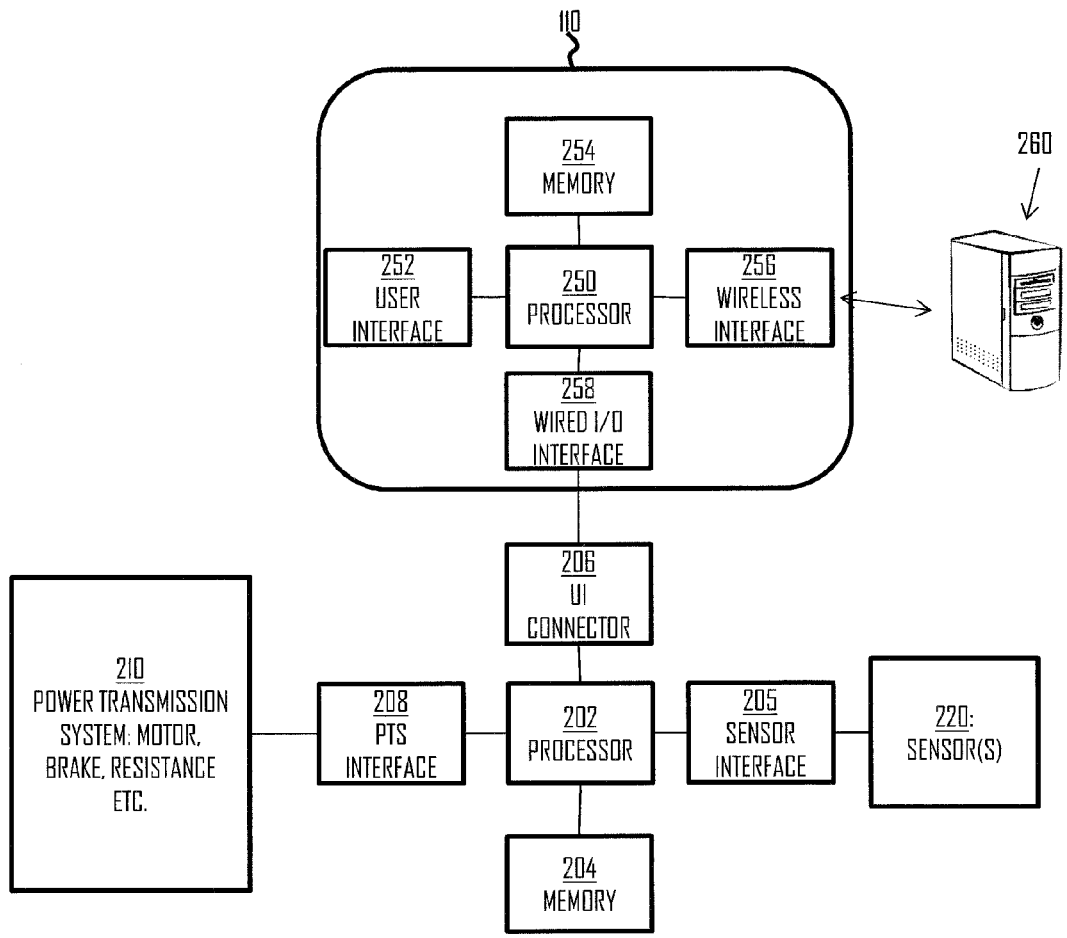

Referring to the portable electronic device 110 in FIGS. 2A and 2B, the portable electronic device 110 may be provided in a separate casing from the gym apparatus 108 and connected to the gym apparatus via the standardised connection. The portable electronic device 110 comprises in its casing a wired input/output (I/O) interface 258 complying with the specifications of the above-described standardised connection, e.g. USB, and enabling the communication with the gym apparatus 108. The portable electronic device 110 may further comprise a user interface 252 comprising a touch-sensitive display screen to display information related to the physical exercise and to receive user inputs. The portable electronic device 110 may further comprise a wireless interface 256 to establish a wireless radio connection to a wireless network. The wireless interface may support at least one of the following radio technologies: IEEE 802.11 (Wi-Fi), a cellular telecommunication technology, and Bluetooth®. The cellular telecommunication technology may comprise any one of the modern cellular technologies including GSM (Global System for Mobile Communications), UMTS (Universal Mobile Telecommunication System), LTE (Long-term Evolution), and LTE-Advanced. In general, the wireless interface 256 may provide the portable electronic device 110 with a network connection to a local area network, the Internet, and/or to external networks. The portable electronic device 110 may further comprise at least one processor 250 and at least one memory 254 including a computer program code, wherein the at least one memory and the computer program code are configured, with the at least one processor, to cause the portable electronic device 110 to process exercise-related measurement data received from the interface circuitry 200 of the gym apparatus 108. The portable electronic device 110 may further comprise a battery, although in some embodiments where the portable electronic device is integrated into the gym apparatus 108, the battery may be omitted.

The memory 254 of the portable electronic device 110 may store an operating system configuring basic operations, managing hardware resources, and providing common services for computer programs executed in the portable electronic device 110. The operating system may be an open source operating system such as Linux, or it may be a commercial operating system such as Microsoft Windows or Windows Phone, Apple iOS, Google Android, Blackberry Tablet OS, or Symbian. The operating system installed on the portable electronic device 110 may be custom-designed for the portable electronic device 110 or a product family of the portable electronic device 110. The operating system may be retail software that may be purchased by a private person as a stand-alone software product without any hardware. Accordingly, the operating system of the portable electronic device 110 need not be custom-designed for the gym apparatus 108, because the communication between the portable electronic device 110 and the gym apparatus 108 is carried out over the standardised connection, and the interface circuitry 200 operates as a mediator between the portable electronic device 110 and the components of the gym apparatus 108 such as the sensor(s) 220 and the power transmission system 210.

In an embodiment, the gym apparatus 108 and uses the portable electronic device 110 to transfer the measurement data to a server computer 260 storing the user's user account. The wireless interface 256 may be used to establish a network connection with the server 260, and the interface circuitry may transfer the measurement data to the server 260 via the portable electronic device 110.

FIG. 3A illustrates an embodiment of low-level signal routing carried out by the interface circuitry 200. By "low-level" is meant physical connections. The interface circuitry 200 may have an electric connection with a measurement circuitry 304 comprised in the gym apparatus. The measurement circuitry 304 may comprise one or more electrodes on a handlebar of the gym apparatus, for example, to measure the user's heart rate, one or more motion sensors, one or more power sensors, and/or other sensors configured to measure physiological measurement data during the physical exercise from the user or from the gym apparatus 108. The measurement circuitry 304 may comprise a hand measurement electronics board including a differential amplifier and a signal path with proper filtering. It may output as data an analog signal that is fed to an analog-to-digital (A/D) converter of the interface circuitry. Alternatively, it may output an A/D converted digital signal that is fed to an input/output (I/O) pin of the processor 202 of the interface circuitry 200. Another option is to make a body composition measurement that measures user's body impedance. In a similar manner, a data signal may be in an analog waveform and fed to the A/D converter of the interface circuitry 200 or, if the measurement circuitry 304 comprises the A/D converter, as a digital signal directly to the I/O pin of the processor 202. In summary, depending on the implementation, the measurement circuitry 304 may comprise the A/D converter to convert analog measurement signals into a digital form. In another embodiment, the A/D conversion is made by the interface circuitry 200.

In an embodiment, the signal lines between the measurement circuitry 304 and the interface circuitry 200 comprise a measurement data signal line and a control line. The measurement data signal line may be used to transfer analog or digital measurement data from the measurement circuitry 304 to the interface circuitry 200, and the control line(s) may be used to indicate which sensor is currently feeding the measurement data. Accordingly, the processor 202 of the interface circuitry is able to separate the measurement data acquired from different sensors and to bundle all the measurement data acquired from a given sensor together and output the measurement data together with an identifier of the sensor associated with the measurement data to the user interface connector 206. The portable electronic device 110 may then process the received measurement data and the identifier and display the measurement data in a form that matches with the display configuration corresponding to the received identifier. For example, the measurement data received from a heart rate sensor may be displayed next to a heart symbol, as illustrated in FIG. 1, while measurement data received from a motion sensor may be displayed in a different manner.

In an embodiment, the interface circuitry 200 comprises a signal line to a proximity receiver 306 which may be configured to communicate with the measurement device 102 external to the gym apparatus 108 and worn by the user, e.g. a heart rate transmitter, a motion sensor worn by the user, a cadence sensor attached to the gym apparatus, etc. The proximity receiver may employ the above-described proximity connection technology, e.g. induction-based communication or near-field communications (NFC) based on radio frequency identification (RFID) technology. The interface circuitry 200 may comprise a digital pulse line connected to the proximity receiver 306, and the proximity receiver 306 may output a digital pulse or a group of digital pulses (in case signal coding is used) whenever the proximity receiver detects a wireless proximity signal from the measurement device 102. The communication over the digital pulse line may be realised with a serial protocol, e.g. RS-232 or USB. With respect to the signal lines used between the proximity receiver and the interface circuitry, the signal lines may comprise one data signal line to convey data from the interface circuitry 200 to the proximity receiver 306, one data signal line to convey data from the proximity receiver 306 to the interface circuitry 200, one signal line for conveying a request-to-send signal used to reserve the data signal line, and one signal line for conveying a clear-to-send signal acknowledging the request-to-send signal and the data signal line reservation.

The proximity receiver 306 may comprise for example a 5 kHz wireless receiver board. A signal it receives may comprise one digital pulse, several digital pulses, or a serial data burst. Communication may be unidirectional or bidirectional depending of the implementation.

In case the coding is used, the coding may be used to identify the sensor type, e.g. pulse may represent the heart rate transmitter, while two pulses may represent the motion sensor. The interface circuitry 200 may thus identify the measurement data received from each measurement device, accumulate the measurement data on the basis of the identifiers, and output the measurement data of a given measurement device together with the corresponding identifier of the measurement device to the portable electronic device 110.

In an embodiment, the interface circuitry 200 comprises a signal line to a radio frequency (RF) module 308 configured to establish a radio connection or connections with measurement devices by using a radio communication protocol such as Bluetooth, Bluetooth low energy, ANT, ANT+, W.I.N.D, ZigBee, etc. The RF module 308 may provide similar data as the proximity receiver together and the connection between the RF module 308 and the interface circuitry 200 may be any one of the connections described above in connection with the proximity receiver 306, and the identifier of the measurement device 102 feeding the measurement data may be acquired according to the specifications of the applied radio communication protocol, e.g. in each data packet the RF module receives from the measurement module. The RF module 308 may establish a bidirectional connection with the measurement devices, which enables the configuration of the measurement devices from the gym apparatus 108 and/or from the portable electronic device 110. For example, the processor 202 of the portable electronic device may control the radio connection and/or the measurement parameters of the measurement device. Upon detecting problems in the received measurement data, the processor 202 may change some of the processing parameters of the measurement device and/or parameters of the radio connection to improve the quality of the measurement. The interface circuitry 200 may thus receive commands from the portable electronic device 110 through the user interface connector 206, change the physical format of the command and output the reformatted command to the RF module 308 and/or to the measurement device through the RF module 308.

In addition to communicating with the measurement device(s), or as an alternative to that, the RF module 308 may be configured to communicate with the user's personal electronic device, e.g. a wrist computer. The personal electronic device may differ from the portable electronic device 110. The interface circuitry 200 may, for example, receive the user's personal training data from the personal electronic device, e.g. name, gender, weight, program of the physical exercise, and heart rate zones. The interface circuitry 200 may output such personal training data to portable electronic device 110 through the user interface connector 206. In an embodiment, the processor 202 may determine initial configuration for the power transmission system 210 on the basis of the program data and output control commands defining the initial configuration to the power transmission system.

Consider now some examples of data transferred through the user interface connector of the interface circuitry and the data line 300 between the interface circuitry 200 and the portable electronic device 110. Data for controlling the power transmission system may be transferred from the portable electronic device 110 to the power transmission system 210 through the interface circuitry 200 and the data line 300. The interface circuitry may receive user-related data from the sensor interface 205 and output it to the data line 300. In another example, the processor may derive control commands for the power transmission system from the user-related data received through the sensor interface 205 and output the control commands to the PTS interface 208. In general, the interface circuitry may collect data from different sources (302, 304, 306, 308), process it in the processor 202 and pack it into a proper format that can be transferred through the user interface connector 206 and the standardised connection. Data formats employed may depend on a data protocol of the connection with the portable electronic device 110 and with the sensors 220. Data returned from the portable electronic device 110 may correspond to the same data protocol, and the data may be converted to an appropriate format of each interface in the processor 202 of the interface circuitry 200.

The measurement circuitry 304, the proximity receiver 306, and the RF module 308 may each be connected to the sensor(s) 220 and to the sensor interface 205 of the interface circuitry 200. In another embodiment, the measurement circuitry 304, the proximity receiver 306, and the RF module 308 are comprised in the sensor interface 205 of the interface circuitry 200 and connected to the sensor(s) 220.

The sensor(s) 220 may provide, for example, user parameters that may be transferred from the sensor(s) 220 through sensor interface 205 to the processor 202 and then through the user interface connector 206 to the portable electronic device.

With respect to the above-described embodiment of transferring the measurement data acquired during the exercise to the server 260, the connection to the server 260 may be realised between the interface circuitry 200 and the server 260 through the portable electronic device 110, as described above, or through the RF module 308 of the gym apparatus 108 or the interface circuitry 200. The processor 202 of the interface circuitry 200 may establish the connection as a transport control protocol/internet protocol (TCP/IP) connection, for example. Other communication protocols may be equally used when establishing an end-to-end connection between the interface circuitry 200 and the server 260. The memory 204 of the interface circuitry 200 may store the server's 260 network address, e.g. a uniform resource locator (URL), or the processor 202 controlling the connection with the server may receive the network address from the measurement device, user's personal electronic device, or from the portable electronic device 110. Upon acquiring the network address, the processor 202 may establish the connection with the correct server and transfer the measurement data to the server. The processor may enable the server to identify to which user the measurement data relates, by transmitting a user's identifier in connection with the measurement data. The user identifier may be an identifier of the user him/herself (e.g. user's unique name or nickname stored in the server) or a device identifier of the user's personal electronic device stored in the server, e.g. a measurement device or a sports watch.

Figure 3B:
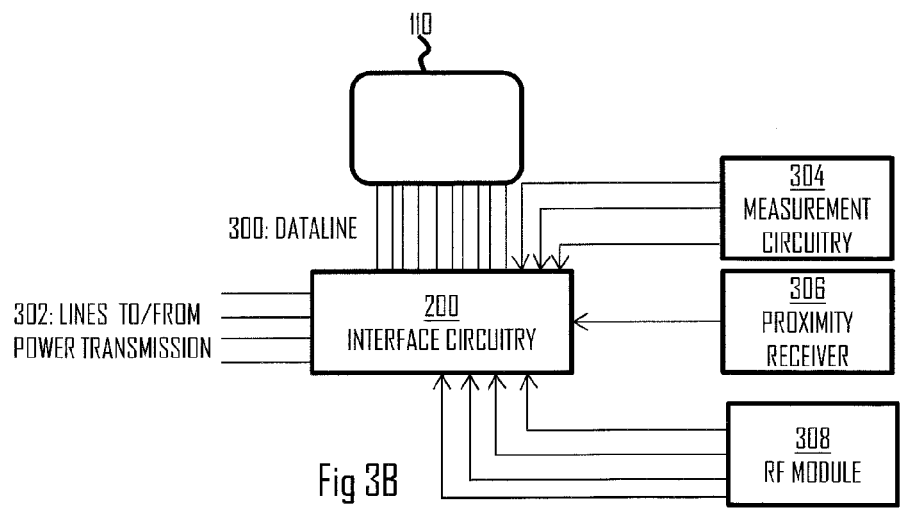

FIG. 3A illustrates an embodiment where the interface circuitry 200, the measurement circuitry 304, the proximity receiver 306, and the RF module are comprised in the same structure. They may be components assembled in the same casing or on the same circuit board, or otherwise contribute to the same structural entity. This is illustrated in FIG. 3A by the dashed line encircling the components 200 and 304 to 308. In another embodiment illustrated in FIG. 3B, one or more of the components 200 and 304 to 308 may be provided as structurally separate from the other components, e.g. in different casings or on different circuit boards.

With respect to the control lines to/from the power transmission 302, consider now some embodiments of data transferred between the interface circuitry 200 and the power transmission system 200. In an embodiment where the gym apparatus 108 is a treadmill, the control commands from the portable electronic device to the power transmission system may be speed up/down commands, incline/recline commands, training program information indicating when an inclination or speed changes, etc. The data from the power transmission system 210 to the portable electronic device 110 may comprise feedback speed information, user's weight information, pressure information indicating user's location on the treadmill, feedback incline/recline values, proximity sensor data indicating whether the user on the equipment or not and so on. At least some of this information may be alternatively provided by the measurement circuitry 304 through the sensor interface 205. In an embodiment where the gym apparatus 108 is an exercise bike, the data forwarded by the interface circuitry 200 from the portable electronic device 110 to the power transmission system may be a resistance value and/or resistance value changes related to the training program, etc. Data from the power transmission system 210 to the portable electronic device 110 may comprise a return resistance value, speed, and/or cadence or the like. In an embodiment where the gym apparatus 108 is an elliptical trainer, the data from the portable electronic device 110 to the power transmission system may be a resistance value and/or resistance value changes related to the training program, etc. Data from power transmission system 210 to the portable electronic device may comprise a return resistance value, speed, and/or cadence or the like. In an embodiment where the gym apparatus is a stepper device, the data transferred from the portable electronic device to the power transmission system 210 may comprise the resistance, and data transferred from the power transmission system 210 to the portable electronic device 110 may comprise the speed, user's weight, step length, etc. In an embodiment where the gym apparatus 108 is a rowing machine, the data transferred from the portable electronic device 110 to the power transmission system 210 may be a resistance value and/or its change according to the training program, and data transferred from the power transmission system to the portable electronic device 110 may comprise a return resistance value, speed (strides/minute), motion length, etc.

Figure 4:
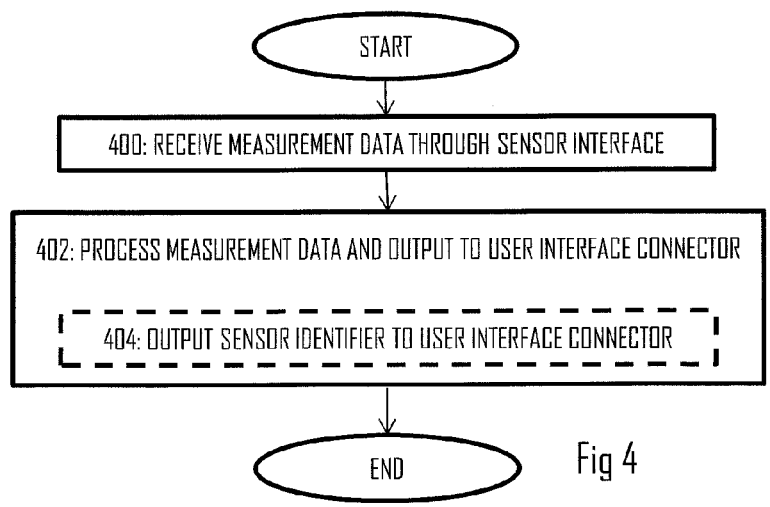
FIGS. 4 and 5 illustrate schematically flow diagrams of examples of processes carried out in the interface circuitry according to some embodiments of the invention.

FIG. 4 illustrates a flow diagram of the operation of the processor 202 when transferring measurement data received from the sensor(s) to the portable electronic device 110. Referring to FIG. 4, the processor 202 of the interface circuitry 200 receives the measurement data through the sensor interface 205 and an identifier of a sensor providing the measurement data in block 400. The sensor may be identified on the basis of the waveform of the measurement data and/or on the basis of a sensor identifier received separately. The processor 202 may stream the measurement data in real time to the user interface connector 206 or it may accumulate the measurement data for a determined time period and, then, transmit the accumulated measurement data in a bundle to the user interface connector 206 (block 402). Depending on an embodiment, the processor 202 may forward only the measurement data if the sensor may be identified without the provision of the identifier, e.g. the portable electronic device 110 receives only one type of measurement data from one sensor. However, the processor 202 may provide the portable electronic device 110 with the sensor identifier associated with the measurement data (block 404).

In an embodiment, the processor 202 of the interface circuitry 200 computes advanced performance data from the signal(s) received through the sensor interface. For example, the processor 202 may compute a heart rate value, an acceleration value, a speed value, or another metric value that represents the measurement data and, then, output the computed value to the user interface connector, with or without the sensor identifier. Other examples of the advanced performance data include a total energy expenditure during the exercise, energy expenditure rates during the exercise, energy expenditure in metabolic component levels comprising fats, carbohydrates and/or proteins, user's maximal oxygen uptake, a fitness parameter, a relaxation estimate characterising the physical or mental relaxation of the user, a training load parameter characterising an effect of the training in terms of physical load, a recovery need parameter indicating a need for recovery as a result of the physical exercise, user-specific heart rate zones, a recovery estimate characterising the user's recovery status, and a dehydration estimate. The advanced performance data may be computed from the received measurement data by using state-of-the-art techniques. In another embodiment, the advanced performance data is computed in the portable electronic device 110.

Figure 5:
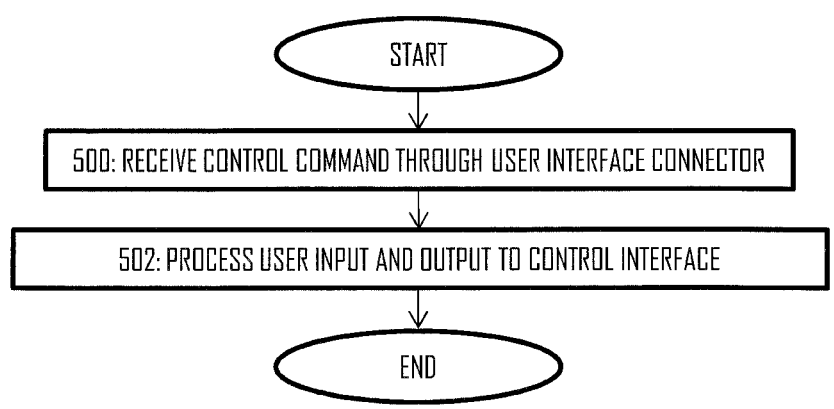

FIG. 5 illustrates an embodiment where the interface circuitry 200 routes commands between the portable electronic device 110 and the power transmission system 210. Referring to FIG. 5, the interface circuitry receives through the user input connector 206 a control command from the portable electronic device 110 (block 500). The control command may originate from a user input, or it may be computed by the portable electronic device on the basis of a predetermined training program and/or measurement data acquired during the physical exercise. In block 502, the processor 202 of the interface circuitry 200 processes the control command. The processing may comprise identifying that the control command is destined to the power transmission system and/or identifying the component of the power transmission system to which the control command is addressed. Then, the processor 202 may output the control command to a signal line connected to the addressed component in the PTS interface 208.

As described above, the interface circuitry 200 may in its simplest form be a simple signal router connected to the sensor(s), the power transmission system 210, and the portable electronic device 110 and configured to route signals between any two of them. Accordingly, the interface circuitry 200 may be considered as providing physical connections between the components comprised in the gym apparatus 108 and connected to the gym apparatus 108 with wired or wireless connections and performing reformatting of signals transferred between the components. The interface circuitry 200 may also configure the establishment of the connections with the sensors 220, e.g. pairing with the sensors and/or with the user's personal electronic device. For example, the processor 202 may control the pairing by causing communication of a sensor identifier over the proximity connection and then configuring the RF module to establish the radio connection with a sensor identified by the received identifier.

In other embodiments, the processor 202 of the interface circuitry 200 is configured to carry out at least some of the application level signal processing by processing payload contents of signals, messages, and/or commands being transferred between the components 220, 210, 110. Above, some embodiments of the application level signal processing have been described, e.g. the processor 202 may compute the advanced performance data, compute control commands for the power transmission system from received personal data, control transfer of the measurement data to the server 260, etc. Yet another embodiment of the higher level processing carried out by the interface circuitry 200 is determining, upon acquiring multiple versions of user's personal data from different sources, the latest version of the personal data and using that in the physical exercise and overwriting obsolete personal data with the latest data. The interface circuitry 200 may gather the personal data for the physical exercise from various sources including the portable electronic device (when it is the user's personal device), the measurement device 102, the server 260, or the user's personal electronic device (e.g. the sports watch). Different sources may provide at least partially the same personal data but with different time labels. The processor 202 may then determine for each type of personal data which source provides the latest (newest) data and use the latest version and discard the older versions. The processor 202 may then output the latest version of the personal data to the sources that provided the older versions so that they may also update their records.

As used in this application, the term "circuitry" refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of "circuitry" applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described above may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

The present invention is applicable to devices designed for use in connection with physical training. The embodiments employ some communication protocols having specifications and elements that develop rapidly. Such development may require extra changes to the described embodiments. Therefore, all words and expressions should be interpreted broadly and they are intended to illustrate, not to restrict, the embodiment. It will be obvious to a person skilled in the art that, as technology advances, the inventive concept can be implemented in various ways. The invention and its embodiments are not limited to the examples described above but may vary within the scope of the claims.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A gym apparatus comprising:
an interface circuitry realized on a single circuit board, the interface circuitry comprising:
  a processing system;
  a power transmission system interface for a power transmission system of said gym apparatus;
  a sensor interface for one or more sensors comprised in said gym apparatus, the sensor interface comprising:
    a measurement circuitry comprising hand measurement electronics including a differential amplifier, a signal path to the processing system of the interface circuitry, and filtering; and
    a radio frequency module arranged to establish a radio connection with a heart rate sensor external to a said gym apparatus and attachable to a user's body; and a standardized user interface connector for connecting the interface circuitry to a casing of a portable electronic device serving as a user interface of said gym apparatus during a physical exercise performed with said gym apparatus, wherein said processing system is constructed and arranged to cause the interface circuitry to process and provide connections between the power transmission system interface, the sensor interface, and the user interface connector, and wherein said portable electronic device is integrated into the gym apparatus and comprises: a communication interface arranged to connect to the standardized user interface connector, a user interface comprising a touch-sensitive display, and an internet browser supporting web applications.

2. The gym apparatus according to claim 1, wherein the user interface connector is a universal serial bus connector.

3. The gym apparatus according to claim 1, wherein the portable electronic device is a touch screen computer.

4. The gym apparatus according to claim 3, wherein the portable electronic device is a tablet computer.

5. The gym apparatus according to claim 1, wherein the sensor interface connects to at least one internal sensor of the gym apparatus.

6. The gym apparatus according to claim 1, wherein the sensor interface connects to a wireless communication circuitry of the gym apparatus.

7. The gym apparatus according to claim 6, wherein the sensor interface connects to at least one of the following wireless communication circuitries: a radio modem and an induction-based proximity receiver.

8. The gym apparatus according to claim 1, wherein the processing system is arranged to cause the interface circuitry to:
receive through the sensor interface measurement data related to a physical exercise and an identifier of a sensor providing the measurement data; and
output the measurement data and the identifier to said portable electronic device through the user interface connector.

9. The gym apparatus according to claim 1, wherein the processing system is arranged to cause the interface circuitry to transfer data with a network server through a said portable electronic device over a network connection.

10. The gym apparatus according to claim 1, wherein the user interface circuitry is further connected to a personal user interface device carried by a user of the gym apparatus.

11. The gym apparatus according to claim 10, wherein the processing system is arranged to cause the interface circuitry to:
acquire measurement data during a physical exercise the user performs with a said gym apparatus; and
output the measurement data and an identifier of a said gym apparatus to the user interface device at the end of the physical exercise.

12. The gym apparatus according to claim 1, wherein the processing system is arranged to cause the interface circuitry to receive a sensor command from the user interface connector and to process the sensor command and forward the sensor command to the sensor interface.

13. The gym apparatus according to claim 1, wherein the processing system is arranged to cause the interface circuitry to process a user input received through the user interface connector and transmit a control command to the power transmission system of said gym apparatus through the power transmission system interface.

14. The gym apparatus according to claim 1, wherein the processing system is arranged to acquire a network address of a server computer storing the user's user account, to establish a network connection with the server computer through the user interface connector and the portable electronic device and to transfer measurement data of the physical exercise to the server computer over the network connection.

15. Gym apparatus according to claim 1, wherein the gym apparatus comprises a socket to receive the casing of a second portable electronic device detachably, wherein the socket comprises a second user interface connector or is connected to the user interface connector of the interface circuitry.

16. Gym apparatus according to claim 1, wherein the portable electronic device further comprises:
a casing covering the portable electronic device and physically separating the portable electronic device from the gym apparatus; and
a processing system constructed and arranged to cause the portable electronic device to:
receive said measurement data received from the interface circuitry and display said measurement data to a user;
determine a control command for the power transmission system of the gym apparatus; and
output the control command to the interface circuitry, wherein the interface circuitry is configured to forward the command to the power transmission system.

* * * * *